United States Patent
Plünnecke (10) Patent No.: US 9,474,851 B2
(45) Date of Patent: Oct. 25, 2016

(54) HOLDER FOR AN INJECTION SYRINGE (75) Inventor: Dieter Plünnecke, Fuldatal (DE)

(73) Assignee: CSL BEHRING GMBH, Marburg (DE)

( * ) Notice: Subject to any disclaimer, the term of this patent is extended or adjusted under 35 U.S.C. 154(b) by 576 days.

(21) Appl. No.: 13/704,019

(22) PCT Filed: Jun. 15, 2011

(86) PCT No.: PCT/EP2011/059904
§ 371 (c)(1),
(2), (4) Date: Jan. 15, 2013

(87) PCT Pub. No.: WO2011/157737
PCT Pub. Date: Dec. 22, 2011

(65) Prior Publication Data
US 2013/0116624 A1 May 9, 2013

(30) Foreign Application Priority Data
Jun. 5, 2010 (EP) .................................... 10165924

(51) Int. Cl.
*A61M 5/00* (2006.01)
*A61M 5/31* (2006.01)

(52) U.S. Cl.
CPC ...... *A61M 5/008* (2013.01); *A61M 2005/3139* (2013.01); *A61M 2205/586* (2013.01)

(58) Field of Classification Search
CPC .. A61M 5/008; A61M 5/001; A61M 5/3129; A61M 2005/3139; A61M 2205/586; A61M 25/02; A61M 5/00; A61B 19/0271
USPC .................................. 206/571; 604/174, 187
See application file for complete search history.

(56) References Cited

U.S. PATENT DOCUMENTS

| 2,455,757 | A |   | 12/1948 | Graybeal |
|---|---|---|---|---|
| 5,925,032 | A | * | 7/1999 | Clements .......................... 606/1 |
| 2004/0122369 | A1 | * | 6/2004 | Schriver ........... A61M 5/14546 604/152 |
| 2004/0249276 | A1 | * | 12/2004 | Nemoto ............ A61M 5/14546 600/432 |

FOREIGN PATENT DOCUMENTS

| DE | 352141 C | 4/1922 |
|---|---|---|
| DE | 20 2005 014 437 U1 | 8/2006 |
| EP | 0 790 063 A1 | 8/1997 |
| EP | 1 486 219 A1 | 12/2004 |

(Continued)

OTHER PUBLICATIONS

International Search Report issued in PCT/EP2011/059904, dated Jan. 27, 2012.

(Continued)

*Primary Examiner* — Theodore Stigell
*Assistant Examiner* — Tiffany Legette
(74) *Attorney, Agent, or Firm* — Birch, Stewart, Kolasch & Birch, LLP (57) ABSTRACT

The present invention relates to a holder for an injection syringe (18), with a housing (12) designed to receive the syringe, with a stand (14) for placing on a supporting surface, and with retaining means (38, 52, 54, 62, 64) for axially and/or radially fixing the syringe (18) on or in the holder, wherein the retaining means (38, 52, 54, 62, 64) are designed in such a way that an outlet (26) of a syringe (18) arranged vertically in the holder comes to lie facing the free end of the stand (14) and at a distance therefrom.

16 Claims, 10 Drawing Sheets

(56) References Cited

FOREIGN PATENT DOCUMENTS

| WO | WO 2005/102416 A1 | 11/2005 |
| WO | WO 2007/012915 A1 | 2/2007 |
| WO | WO 2010/054290 A1 | 5/2010 |

OTHER PUBLICATIONS

International Preliminary Report on Patentability and English translation of Written Opinion issued Jan. 3, 2013, in PCT International Application No. PCt/EP2011/059904.

* cited by examiner

HOLDER FOR AN INJECTION SYRINGE

The present invention relates to a holder for a syringe for self-medication purposes, in particular for placing on a supporting surface.

Particularly in the context of intravenous or subcutaneous administration of medicaments, the active substance, which in most cases is liquid, is delivered to the body tissue using a syringe or comparable injection devices. Particularly in self-medication or home-based therapy, medicines of this kind require suitable training of the patient. For example, if a product for treating hemophilia is to be administered, this is in most cases done using what is called a butterfly cannula.

A patient applies this to the inner aspect of his elbow, for example. However, the patient then has only one hand available for the actual injection procedure. A further consideration is that the product to be administered has a higher viscosity than water, such that the patient has to apply considerable force to a syringe plunger in order to inject the active substance. This maneuvering of the injection syringe with one hand is quite awkward and difficult. In particular, there is the danger that a fluid-conveying hose, which connects the syringe outlet to an injection needle, will become kinked during the injection procedure, which makes delivery of the product even more difficult.

It should also be remembered that hemophiliac patients in particular already suffer from secondary diseases and often have limited mobility and dexterity. Stiff joints, especially in the area of the forearms and hands, can make self-medication very difficult.

Therefore, the object of the present invention is to make available a holder for an injection syringe, specifically a holder which permits simple, safe and reliable injection and facilitates the handling of an injection syringe, or of an injection set comprising an injection hose, a needle and a syringe.

The object of the invention is achieved with the aid of a holder according to independent claim 1. Individual advantageous embodiments of the invention form the subject matter of the dependent claims.

The holder according to the invention is designed in particular for an injection syringe. It has a housing designed to receive the syringe, and a stand for placing the holder on a supporting surface. Moreover, the holder is provided with retaining means for axially and/or radially fixing the syringe on or in the holder. The retaining means are designed in such a way that an outlet of the syringe in the holder is arranged facing the free end of the stand and at a distance therefrom, that is to say comes to lie at a suitable distance from the supporting surface on which the holder is to be placed. In particular, provision is made for the retaining means of the holder to be designed to fix a syringe inside or on the holder such that, when a holder is placed on a supporting surface, the syringe outlet is oriented toward the supporting surface but at a distance therefrom, and the syringe in the holder is arranged vertically, i.e. substantially parallel to the axial direction of the stand and of the holder.

The possibility of placing the holder almost perpendicularly on a supporting surface already simplifies the handling of the syringe for injection purposes. For example, the user can grip the holder with four fingers, while using the thumb to apply a downwardly directed injection force to the retracted syringe plunger. It proves advantageous here that the syringe holder can be safely placed on a supporting surface and that the forces to be applied to the syringe plunger for injection purposes can be diverted via the syringe body into the holder and, finally, onto or into the supporting surface. In cases where the user is unable to apply the necessary injection force with his thumb alone, the holder also makes it possible to use other parts of the body, for example the flat of the hand, to apply pressure to the syringe plunger, without increased danger of kinking the hose that fluidically connects the cannula and the syringe to each other.

The stand is advantageously designed for placing on a substantially flat supporting surface, for example a table. For this purpose, for example, the stand can have a set-down edge which extends at least in part about the periphery and which lies substantially in the plane perpendicular to the longitudinal direction of the syringe.

According to a first preferred embodiment of the invention, provision is therefore made that the retaining means provided on the holder for the syringe allow the syringe to be axially fixed in or on the holder in such a way that the distance of the syringe outlet from the end of the stand corresponds at least to the axial extent of a hose attachment piece plus a minimum hose bend radius at which the hose in fluid connection with the syringe outlet remains open to fluid. This has the effect that the hose to be arranged on the syringe outlet is as it were freely suspended in the holder receiving the syringe. In this way, kinking of the fluid-carrying hose is effectively prevented.

The holder is advantageously suitable for receiving syringes of different sizes. In particular, the holder should be designed for 5-milliliter, 10-milliliter or 20-milliliter disposable syringes. Depending on the preferred syringe type, the distance between the syringe outlet and the end of the stand is intended to be adapted, or is adapted, to the corresponding hose attachment piece and the corresponding hose diameter or minimum hose bend radius. Given his specialist knowledge and his familiarity with the characteristic features of corresponding syringes and hoses, e.g. the length of the syringes and of the attachment pieces and the diameter and flexibility of the hose, a person skilled in the art is able to do this without himself having to be inventive.

According to a development of the invention, provision is also made that the housing of the holder, at its upper end portion directed away from the stand, has a radially outwardly protruding contact flange, which is arranged at least in part about the periphery. This contact flange can effectively prevent the housing from slipping through the user's hand that surrounds the housing. In scenarios where an injection force is to be applied to the syringe plunger by means of the thumb, the other four fingers of the hand surround the housing of the holder. The radially outwardly protruding contact flange, arranged at least in part about the periphery, preferably comes to lie on the side of an index finger directed toward the thumb.

According to a development of the invention, provision is also made that the housing widens radially toward the stand. It is particularly preferable that the housing has an at least partially cylindrical main structure provided with a grip surface on the outside. The grip surface itself can be adapted, for example, to the ergonomics of a human hand. For example, it can have an appropriate surface structure, for example a ribbed arrangement adapted to the individual fingers of a human hand. Alternatively, it can of course also have a substantially smooth contour, for example a circular or oval contour.

The radial widening of the housing improves the stability of the housing on the supporting surface. For example, provision can be made that the housing radially widens toward the stand either conically or otherwise. In this way, even when very high injection forces are applied, it is possible to largely avoid, or indeed eliminate, accidental toppling of the holder or kinking of the syringe hose during an injection procedure.

In a particular embodiment, the housing, the stand and/or the contact flange lying opposite the stand are formed in one piece. In this case, provision is preferably made to produce the housing, the stand and/or the contact flange in the form of a single injection-molded component, preferably an injection-molded plastic component. The design as an injection-molded plastic component is relatively simple and inexpensive.

Moreover, according to a preferred embodiment of the invention, provision is made that the housing has a radially accessible seat for insertion of the syringe into the housing. Considering the cylinder symmetry of the syringe, or of the syringe body that receives the medicament, provision is thus made for the syringe to be inserted into the seat of the housing transversely with respect to the longitudinal direction of the syringe, that is to say transversely with respect to the axial direction. Accordingly, the housing does not have strict cylinder symmetry and is instead formed only part way round the circumferential direction, being designed for example as a cut-open hollow cylinder toward the insertion opening provided for the syringe, which cut-open hollow cylinder can be closed by means of a separate closure mechanism after insertion of a syringe and thus fixes the latter.

Alternatively or in addition to this, however, it is also conceivable to insert the syringe into the holder from above in the axial direction, that is to say in the longitudinal direction of the syringe, until the syringe comes to lie, with its outwardly protruding retaining projections formed at the upper end of the syringe body, on abutment surfaces or bearing surfaces provided for this purpose on the holder. The syringe would then in some cases be fixed on the holder only unidirectionally in the axial direction, namely in the injection direction, with the holder itself functioning as a hollow cylindrical seat for the syringe body.

For the invention, provision is preferably made that the holder can receive syringes of different sizes. The holder should in particular be designed for 5-milliliter, 10-milliliter or 20-milliliter disposable syringes and should be able to fix all syringe formats, or at least the three syringe formats mentioned, both in the radial direction and in the axial direction for injection purposes. In this connection, it proves advantageous if at least one retaining wing is mounted pivotably in the syringe seat of the holder, which at least one retaining wing can be brought into clamping contact with the syringe body when the syringe is inserted into the seat, i.e. with which at least one retaining wing the syringe can be clamped into the holder. The at least one retaining wing makes available a kind of radial locking mechanism for the syringe and ensures that all of the aforementioned syringe sizes, each with different diameters, can be fixed in the syringe seat of the holder.

Provision is advantageously made that the at least one retaining wing is mounted on a pivot axle extending substantially parallel to the axial direction of the holder or parallel to the longitudinal extent of the syringe, under the effect of at least one spring element, preferably a torsion spring. Thus, provision can be made to pivot the retaining wing counter to the spring force during insertion of the syringe, with the result that, when an end position of the syringe in the holder is reached, the retaining wing, with the aid of the retaining force applied by the spring, keeps the syringe in the predetermined position, at least in the axial direction.

According to a preferred embodiment, two retaining wings are provided, which extend parallel to each other, are articulated pivotably on the holder and, depending on the pivoting position, form a syringe seat of variable size. The provision of two retaining wings means that syringe bodies of different sizes can easily be fixed in the holder. It also proves advantageous if the retaining wings have at least in some areas, in the plane perpendicular to the axial direction, that is to say perpendicular to the plane of their pivot axle, a curvature adapted to the syringe body. Seen from the direction of the seat, the curvature of the retaining wings is preferably convex from the inside, such that the syringe body, which is of typically round design in the circumferential direction, comes to bear on the retaining wings across the greatest possible surface area. Depending on the preferred syringe type, the curvature of the retaining wings is to be adapted to the curvature of the syringe body, or it is adapted thereto.

According to another preferred embodiment of the invention, provision is further made that the at least one retaining wing, at an end portion opposite its pivot axle, i.e. at its free end portion, has a substantially radially outwardly protruding end portion, which functions as an insertion aid for the syringe. Seen in the direction in which the syringe is fitted, the retaining wing tapers inward before forming a concavely curved seat for the syringe body.

During the insertion of the syringe, the end portion widening radially toward the free end of the retaining wings not only serves as an insertion aid but can also ensure, during insertion of the syringe body into the seat, that the retaining wings pivot outward and thus only then free the seat for the syringe body. After the syringe body with its full radius has passed this narrowing, the retaining wings can pivot back in the direction of their original configuration, under the effect of the retaining force provided by the torsion spring, and can clamp the syringe body between themselves.

According to another advantageous embodiment of the invention, provision is further made for at least one retaining means to be designed in the form of a closure piece mounted pivotably or rotatably on the housing, such that the seat provided for the syringe can be closed by means of the closure piece. A configuration of this kind is provided particularly if the housing of the holder is only cylindrical in part and open to one side, and it is designed for radial insertion of the syringe and ensures that, in this embodiment too, the syringe is fixed in the holder.

In a preferred embodiment, the closure piece is designed as a flap-like closure which is pivotably articulated on one side of the syringe seat and, after insertion of the syringe into the seat, can be pivoted to the opposite cheek of the housing and fixed there.

The fixing is preferably provided here by a locking mechanism composed of housing cheek and pivotable closure piece. The closure piece itself is preferably designed as a locking means that at least in part encloses the syringe seat in the circumferential direction of the housing and in the longitudinal direction of the syringe. In other words, the closure piece is designed as a locking means which at least in part encloses the seat in the circumferential direction of the housing and in the longitudinal direction of the syringe and which engages with a mating locking means arranged on the outside of the housing. In order to close the syringe seat, it cooperates with a mating locking means arranged on the outside of the housing or on the corresponding housing cheek. Although the syringe can already be fixed on the holder, as seen in the radial direction, with the aid of the at least one retaining wing, the closure piece arranged pivotably on the housing forms a further safety measure against inadvertent release of the syringe from the housing or from the holder.

According to another advantageous embodiment of the invention, provision is further made that the closure piece mounted pivotably on the housing has, on its inner face directed toward the syringe, at least one toothed surface or toothing designed to engage with a correspondingly formed beveled surface or chamfer at the end of the at least one retaining wing, in such a way that the retaining wing pivots radially inward toward the syringe under the action of a radially inwardly directed force applied to the closure piece. In other words, the closure piece engages on the inside with the radially outwardly directed free end portion of at least one retaining wing or preferably two retaining wings, wherein an inwardly directed pressure applied to the closure piece causes the retaining wing to pivot radially inward and can thus bring about a clamping action between retaining wing and syringe.

It proves particularly advantageous here if the closure piece has two surface segments which are arranged next to each other in the circumferential direction and connected flexibly to each other and on each of which an inner toothed surface engages with a beveled surface at the end of a retaining wing. The two surface segments of the closure piece are arranged lying next to each other, as seen in the circumferential direction, and are able to pivot relative to each other along an axis extending in the axial direction. By virtue of this pivotability or bendability of the closure piece, each of the inward and at least partially toothed surface segments can exert a radially inwardly directed force on the retaining wings arranged pivotably in the seat. In this way, it is also possible for one and the same holder to be used to fix syringes of different sizes.

In an alternatively preferred embodiment, the closure piece is designed to be rotatable about the axial direction in relation to the housing, wherein the closure piece is designed with an area which, after partial rotation about the longitudinal direction of the syringe, fixes the syringe in the seat of the housing. In other words, the closure piece, after partial rotation, serves to fix the syringe in the seat of the housing and prevent the syringe from sliding or from slipping out.

The rotatable closure piece is advantageously designed to rotate perpendicularly with respect to the axial direction of the holder and about the longitudinal axis of the syringe. Particularly preferably, the rotatable closure piece is designed in one piece as a screw cap.

For example, the rotatable closure can be designed as a kind of open ring which radially encloses the syringe seat at least in part and has an opening and which, after insertion of the syringe into the seat, is rotatable about the longitudinal direction of the syringe, as a result of which the opening in the ring is laterally rotated and, in this way, the syringe is fixed in the seat. The rotatable closure piece proves especially easy to handle, particularly with one hand, and is therefore particularly advantageous.

In another preferred embodiment of the holder, provision is further made that the closure piece only partially covers the area of the syringe seat as seen in the axial direction. In particular, the lower portion of the syringe directed toward the stand should not be covered by the closure piece, and instead it should remain visible so that the user can visually check the filling level of the syringe during the injection procedure.

Moreover, for the invention, provision is preferably made that the at least one retaining wing and/or the housing itself at its upper end portion directed away from the stand and/or the closure piece located at the upper end portion of the housing directed away from the stand has/have at least one slit or a bearing for a radially outwardly protruding retaining projection or two diametrically radially outwardly protruding retaining projections of a syringe, in order to fix the syringe axially on the holder, at least as seen in the injection direction.

For the slit provided in the upper portion of the retaining wings, an insertion bevel can further be provided for the retaining projections of the syringe, such that, during insertion of the syringe into the seat, a clamping action can also already be obtained in the area of the retaining projections and the slits on the retaining-wing side. If receiving slits for the syringe-side retaining projections are already provided in the retaining wings, the syringe can be fixed bidirectionally on the holder in the axial direction.

In embodiments of the holder without retaining wings or without slits in the retaining wings, it may however also be sufficient if the at least in part circumferentially formed housing of the holder forms a bearing for the syringe-side retaining projections, at least slightly below the radially outwardly protruding contact flange. Thus, when the holder is placed on a supporting surface, the syringe is fixed solely by its weight and, when an injection force is applied that acts on the syringe plunger, it is axially fixed with its retaining projections on the housing-side bearing, for example by being supported thereon.

Further aims, features and advantageous configurations of the invention are explained in the following description of illustrative embodiments, with reference to the figures. All of the features described in the text and also depicted in the figures form, both individually and in any meaningful combination with one another, the subject matter of the present invention.

Figure 1:
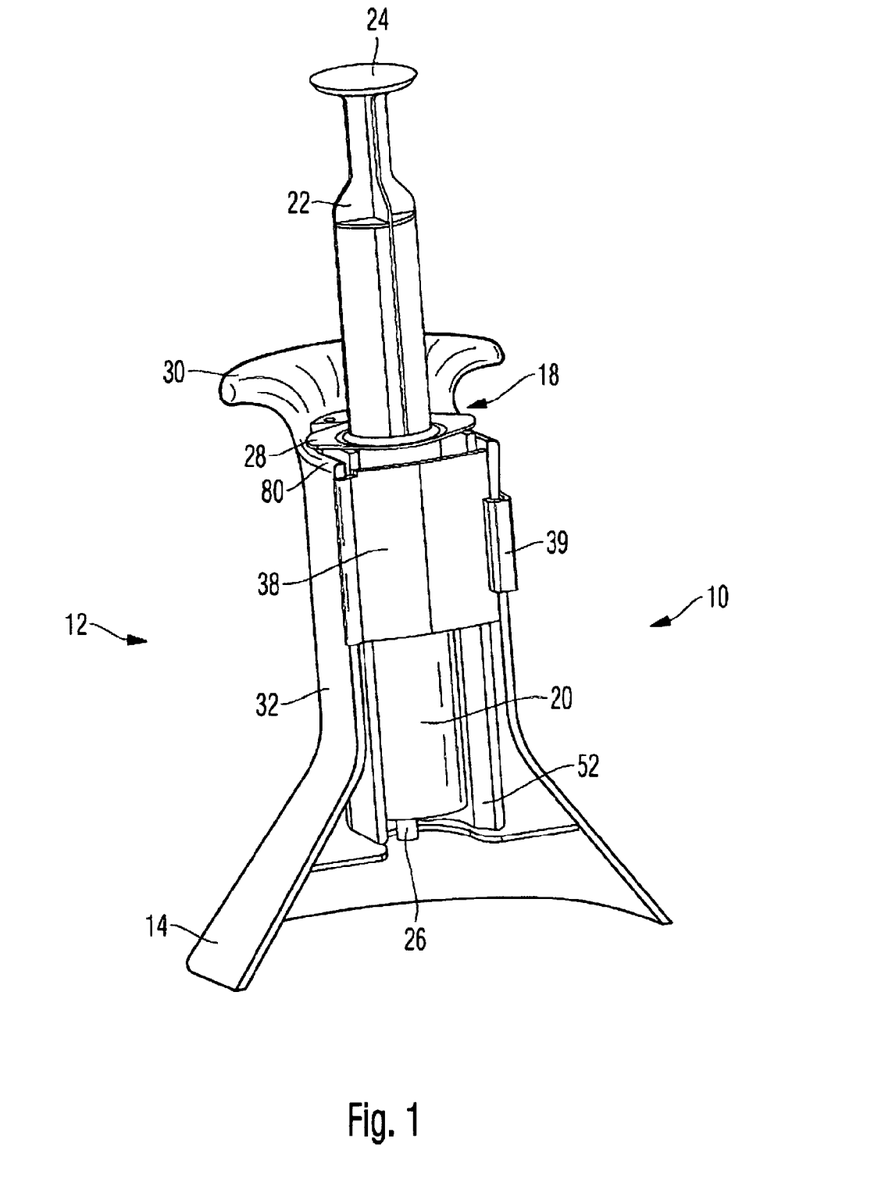
FIG. 1 shows a perspective view of a syringe holder in a first embodiment, with the closure closed.
Figure 2:
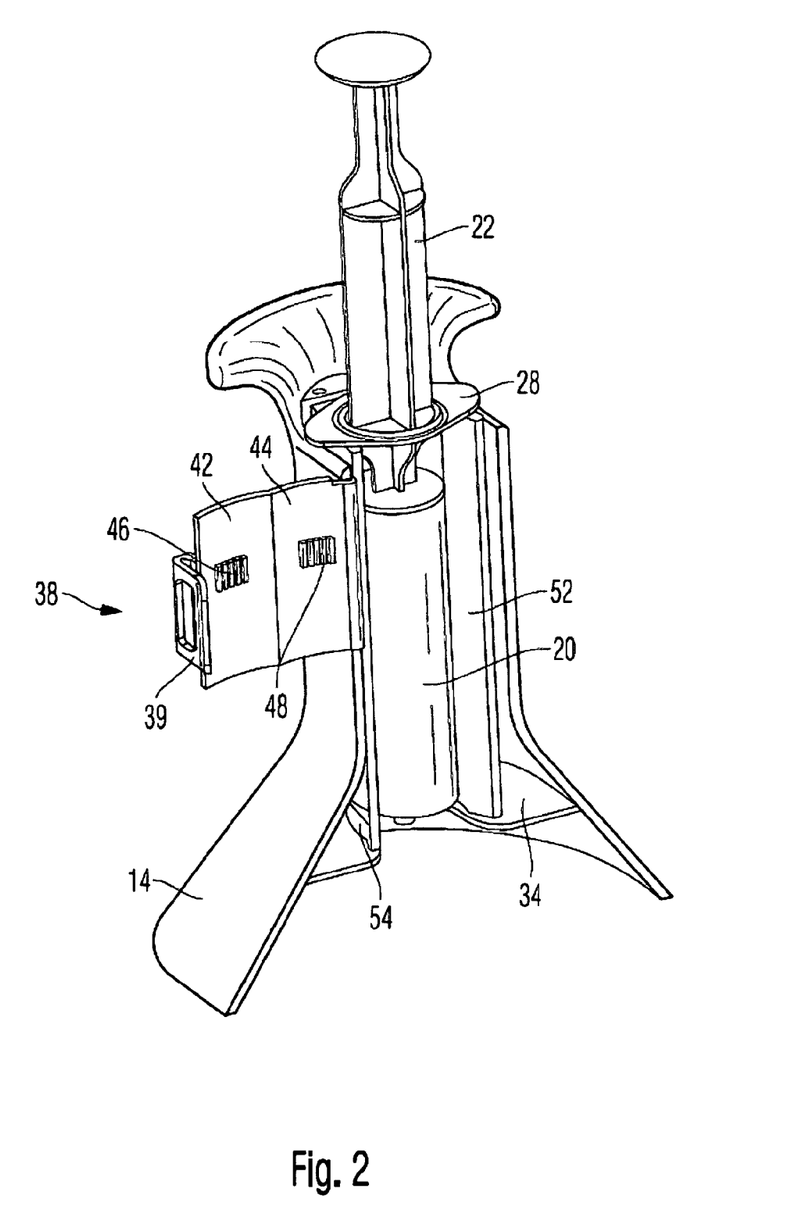
FIG. 2 shows the syringe holder according to FIG. 1 with the closure opened.
Figure 3:
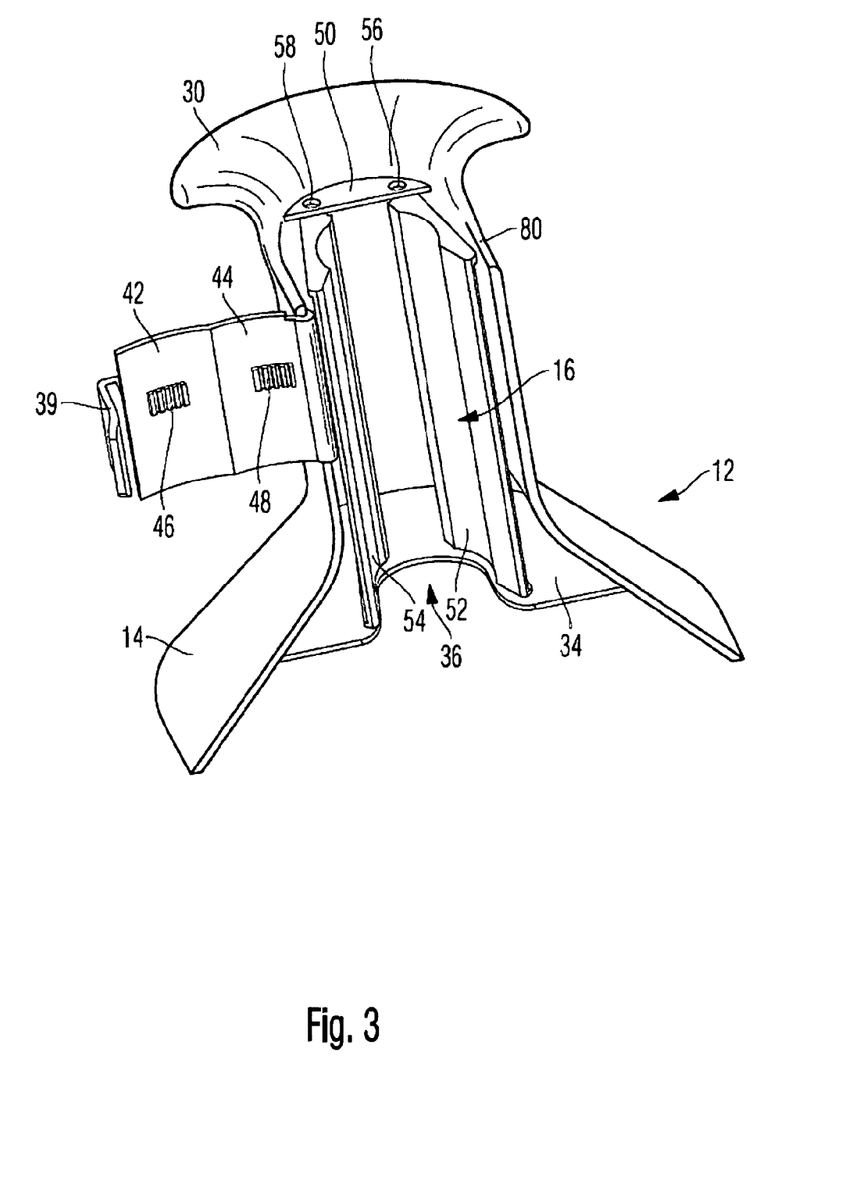
FIG. 3 shows the holder according to FIG. 2 without an inserted syringe.
Figure 4:
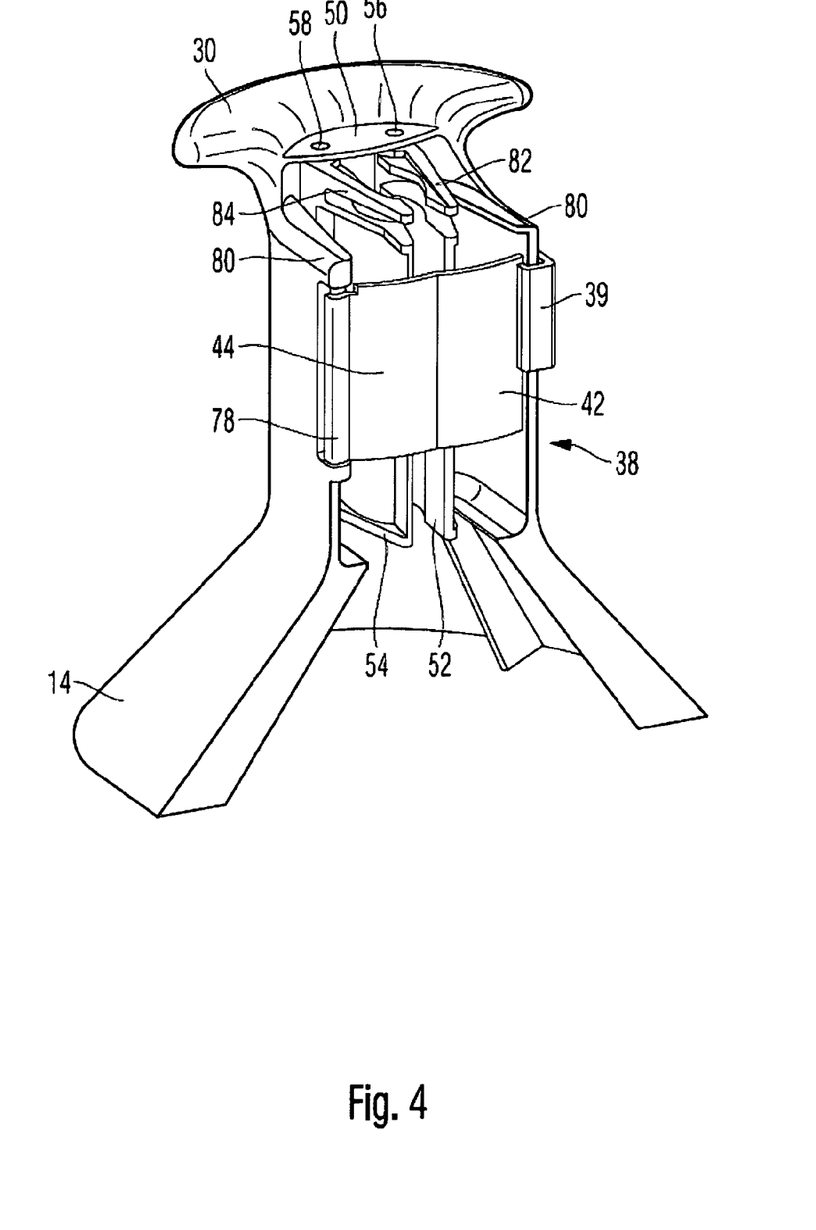
FIG. 4 shows a perspective view of a further embodiment of a holder, with retaining wings slit in the radial direction.

A holder 10 for receiving an injection syringe 18 is shown in FIGS. 1 to 3. The holder 10 has a seat 16, for example for a disposable syringe 18 which, by way of example, has a substantially cylindrically symmetrical syringe body 20 and a syringe plunger 22 axially movable therein. At the end directed away from the syringe outlet 26 of the syringe body 20, the syringe plunger 22 has a pressing or forcing surface 24 via which, for example, the user can use his thumb to subject the syringe plunger 22 to the force needed to inject a liquid.

The holder itself is designed as an injection-molded component, preferably from thermoplastic. The holder 10 has a syringe housing 12 which, toward the bottom, has a radially widening, for example conically extending stand 14, and, at the top toward the syringe plunger 22, has a radially outwardly protruding contact flange 30. Between these, the housing 12 has a grip surface 32. The latter can be ergonomically adapted, for example, to the inner contour of a hand. For injection purposes, it is advantageous if the user applies pressure to the pressing piece 24 from above using his thumb, and if the side of the index finger directed toward the thumb is placed for support on the underside of the radially protruding contact flange 30.

By means of the conically or radially widening stand, the entire holder 10 can be placed safely on a supporting surface (not shown explicitly in the figures). This facilitates the injection procedure and allows the user to apply in a controlled manner the force needed for a slow and smooth injection. It is essential here that the syringe outlet 26 comes to lie at an axial distance from the supporting surface on which the holder 10 is to be placed. In this way, a hose piece, connected fluidically to an injection device passing into the body tissue, can be coupled as it were in a freely suspended manner to the outlet 26 of the syringe 18. Standardized connector components are preferably used, for example Luer lock couplings.

In the axial direction, which runs substantially in the vertical direction in all of FIGS. 1 to 8, the syringe 18 that comes to lie in the seat 16 is supported by its retaining projections 28, which protrude radially from the syringe body 20, on an upper end portion 80 of the housing 12. This end portion 80 functioning as a bearing is arranged slightly below the contact flange 30. This is advantageous to the extent that users with a relatively short thumb are also able to easily actuate a plunger 22 of a relatively large syringe, for example of a 20-ml syringe, for injection purposes.

As can be seen in FIG. 3, the injection-molded housing 12 has, in the area of the conical widening of the stand 14, a web plate 34 which, on the one hand, increases the torsional rigidity and stability of the housing 12 and, on the other hand, can function as a seat for the pivot axles 56, 58 of the two retaining wings 52 and 54. The retaining wings 52, 54 arranged pivotably inside the seat 16 are articulated at the bottom on the web plate 34 and at the top on a crosspiece 50. Any spring elements 76 acting on the retaining wings 52, 54 are not explicitly shown in FIGS. 1 to 3. Approximately flush with the seat 16 formed by the retaining wings 52, 54, a through-opening 36 is provided in the web plate 34 lying at the bottom, wherein the syringe outlet 26 or, depending on the syringe size, also the syringe body 20 can come to lie within said through-opening 36.

FIG. 3 also shows the inner face of the pivotable closure 38 which is articulated on a side cheek of the cylindrical housing portion so as to pivot about an axle 78 and which, with the aid of a locking means 39, can be locked on the opposite housing cheek (arranged on the right-hand side in FIG. 3) and on a mating locking means 40 arranged there. The closure 38 is divided into two surface segments 42, 44 which, on at least part of their inner face, have an axially extending and circumferentially extending toothing or toothed surface 46, 48.

The two surface segments 42, 44 are flexurally elastic with respect to each other and pivotable. A kinking or bending axis 70 (shown separately in FIG. 5) runs between the two surface segments.

Figure 7:
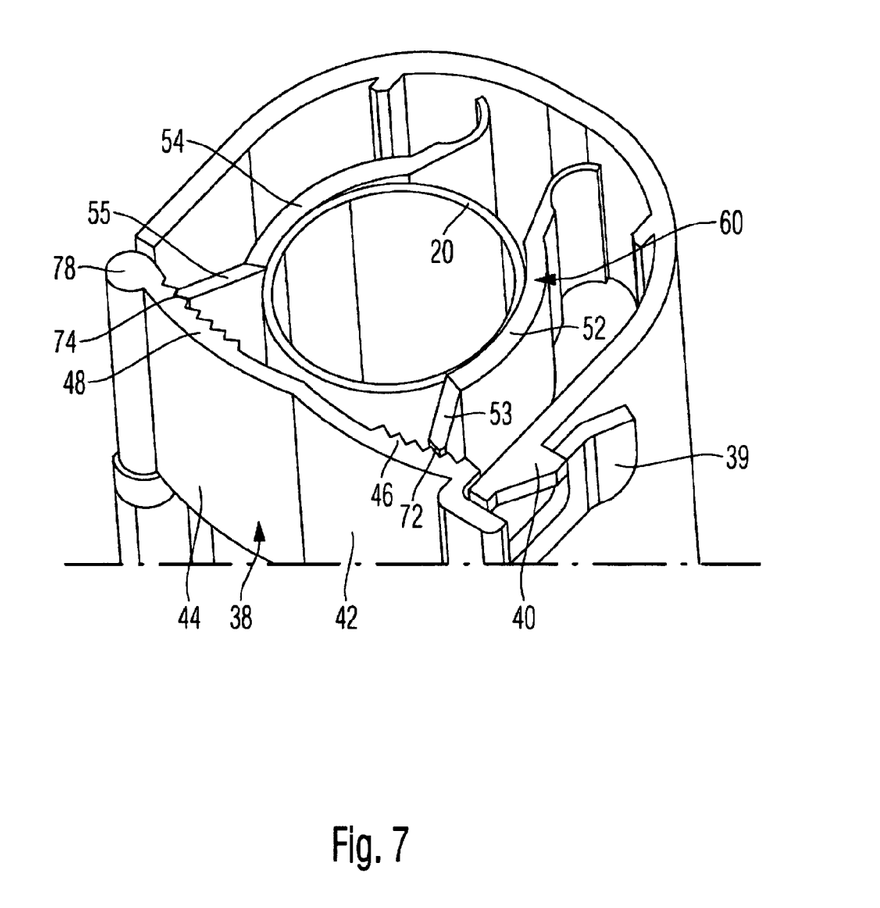
FIG. 7 shows a perspective view of a cross section through the holder according to FIGS. 4 to 6 at the height of the toothing provided on the closure.

When it reaches its closure position illustrated in FIG. 7, a closure tab 39 of the closure 38 locks onto a mating locking element 40 formed on the side cheek of the housing. It can also be seen here how the radially inwardly facing toothed surfaces 46, 48 engage with the correspondingly designed chamfered end portions of the retaining wings 52, 54. If, for example, a radially inwardly directed pressure is applied to the surface segments 42, 44 of the closure 38, this has the effect that the retaining wings 52, 54 are pressed radially inward, by the mutual meshing of toothed surface 46, 48 and chamfer 72, 74, to form a clamping effect with the syringe body 20. In this way, the holder 10 can be used universally for different sizes of syringes and for different syringe diameters.

Compared to the embodiment according to FIGS. 1 to 3, the only real difference in the embodiment according to FIGS. 4 to 8 lies in the differently configured retaining wings 52, 54, even though these have been designated by the same reference numbers for simplicity. As can be seen from FIGS. 5 and 6, the retaining wings 52, 54 in this case each have a slit 62, 64 which lies approximately at the height of the bearing 80 of the housing 12 and into which the diametrically opposite retaining projections 28 of the syringe body 20 can be inserted in the radial direction.

Figure 5:
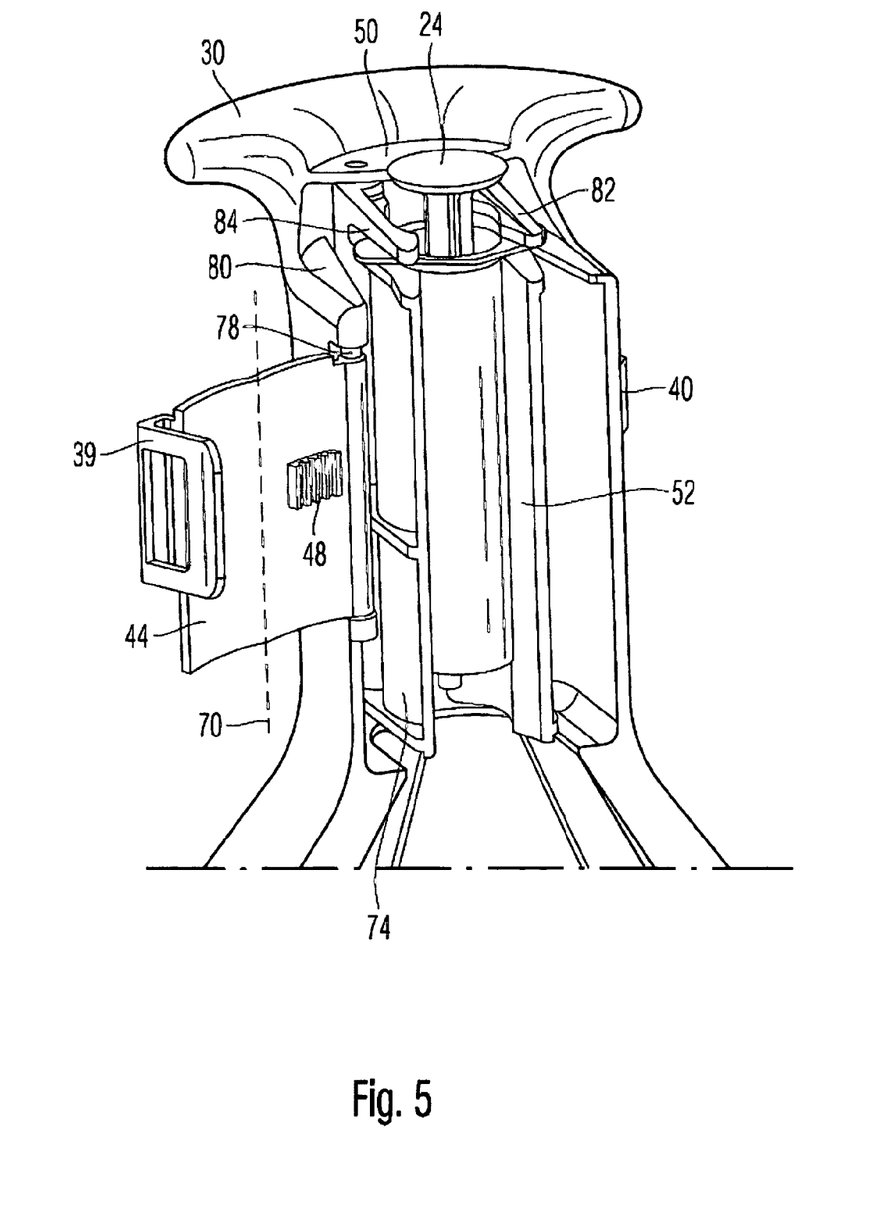
FIG. 5 shows the holder according to FIG. 4 with an inserted syringe.
Figure 6:
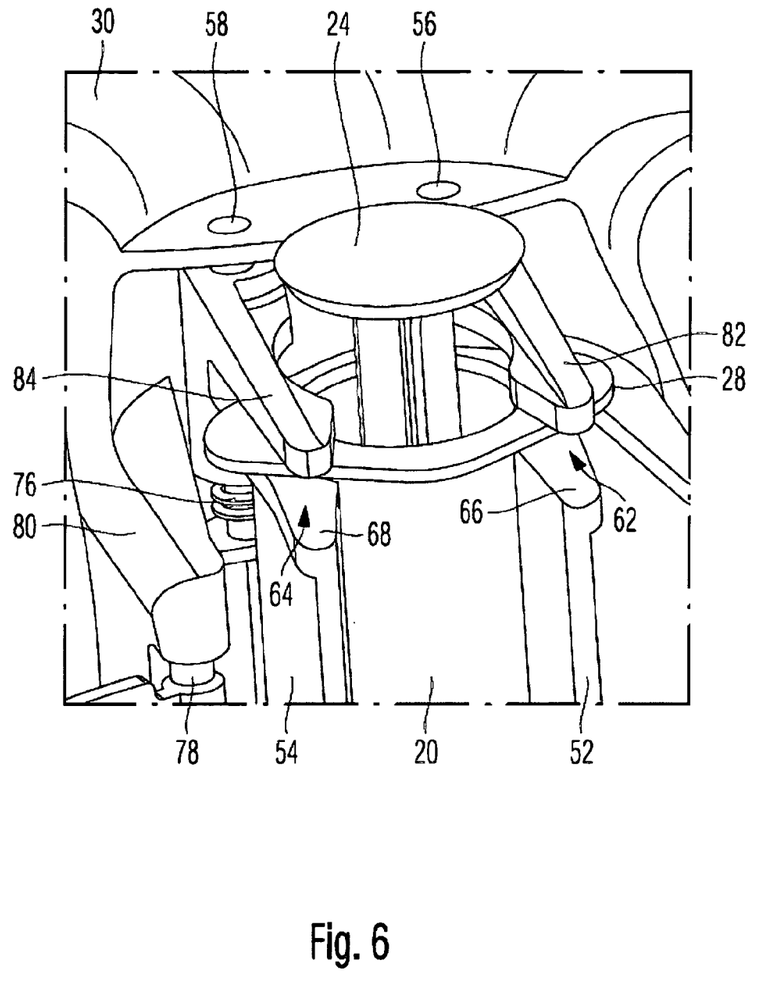
FIG. 6 shows an enlarged detail of the syringe holder according to FIG. 5.

For easy insertion, provision can in this case be made that the slits 62, 64 are provided with an insertion bevel 66, 68. Seen in the axial direction, the retaining wings 52, 54 are to this extent divided in two, the upper end of the retaining wings now being formed in each case by a peg 82, 84 designed flush with the actual wing 52, 54.

Figure 8:
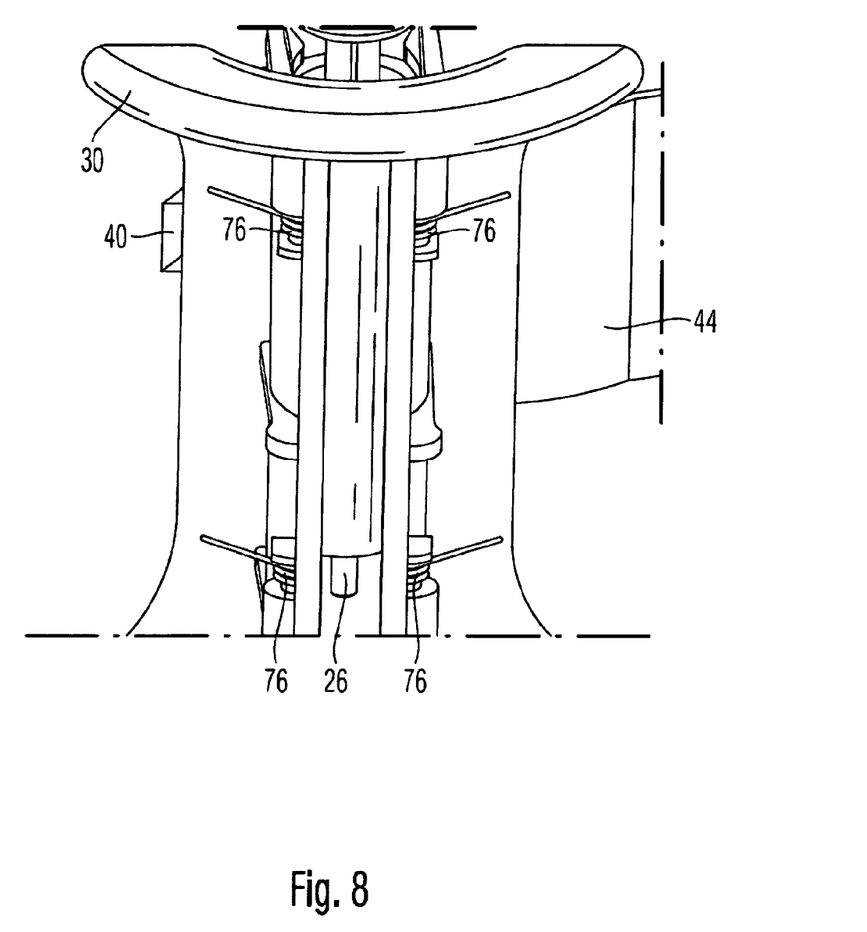
FIG. 8 shows a partially cutaway rear view of the holder according to FIGS. 4 to 7.

FIGS. 6 and 8 also show various torsion spring elements 76, by means of which the retaining wings 52, 54 are articulated pivotably on the holder under spring pretensioning.

It can also be seen from FIG. 7 that the retaining wings 52, 54 are concave in part, so as to be able in particular to form a press fit 60 with the substantially cylindrical syringe body 20. The radial end portion of the retaining wings 52, 54 lying at a distance from the respective pivot axles 56, 58 is preferably designed to protrude radially outward in order to facilitate the engagement of the cylindrically symmetrical syringe body 20. For example, the two retaining wings 52, 54 bear directly on each other prior to insertion of a syringe 18. The two radially outward ends 53, 55 of the respective retaining wings 52, 54 form a kind of insertion bevel for the syringe body 20.

If, for example, the syringe is pressed into the seat 16, this kind of radially inwardly directed movement of the syringe body 20 causes the retaining wings 52, 54 to pivot open. As soon as the syringe 18 reaches its end position shown in FIG. 7, the retaining wings 52, 54 pivot radially inward again. By means of the closing of the closure piece 38 and the described mutual engagement of the teeth 46, 48 and the end surfaces 72, 74 of the retaining wings 52, 54, it is possible to produce a sufficient press fit 60 between retaining wings 52, 54 and syringe body 20 and to securely fix the syringe in the holder 10.

Figure 9:
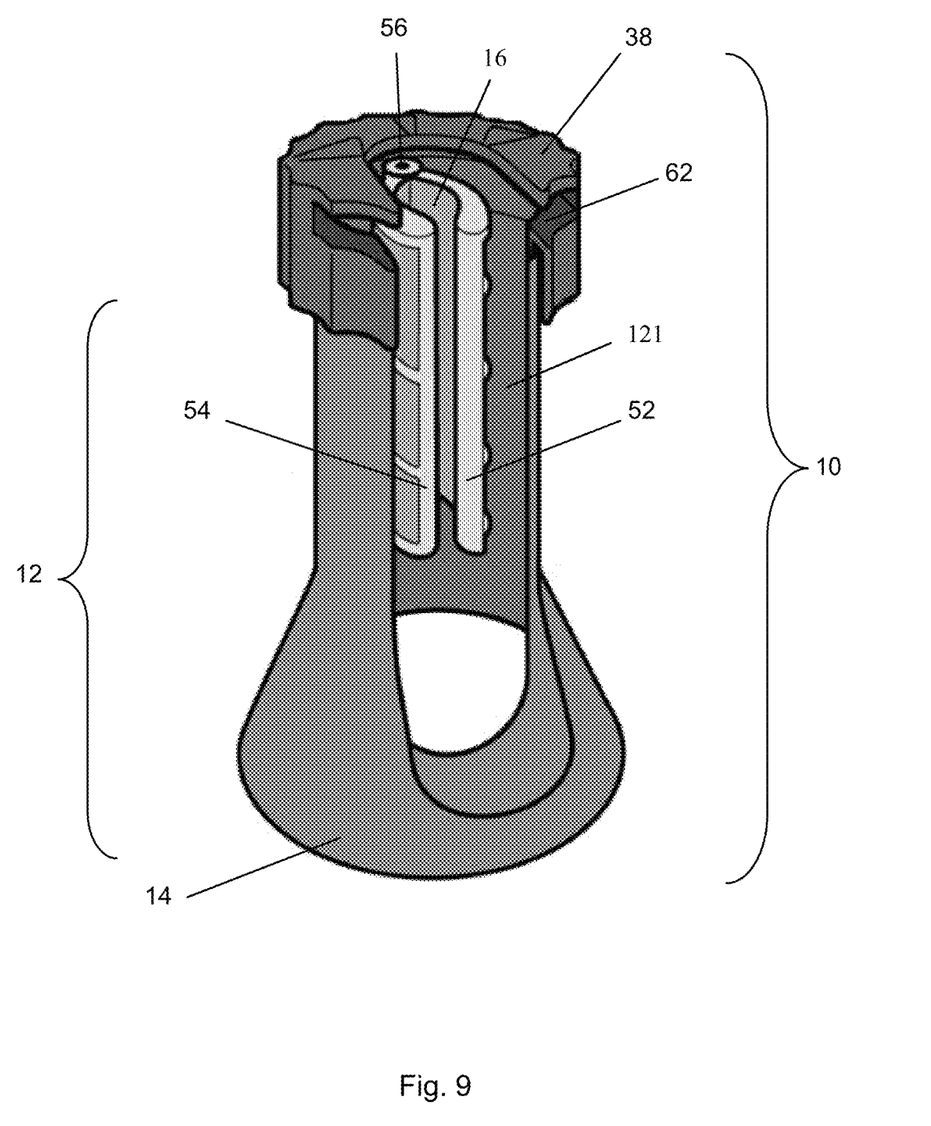
FIG. 9 shows a perspective view of a syringe holder in a further embodiment with a rotatable and opened closure.
Figure 10:
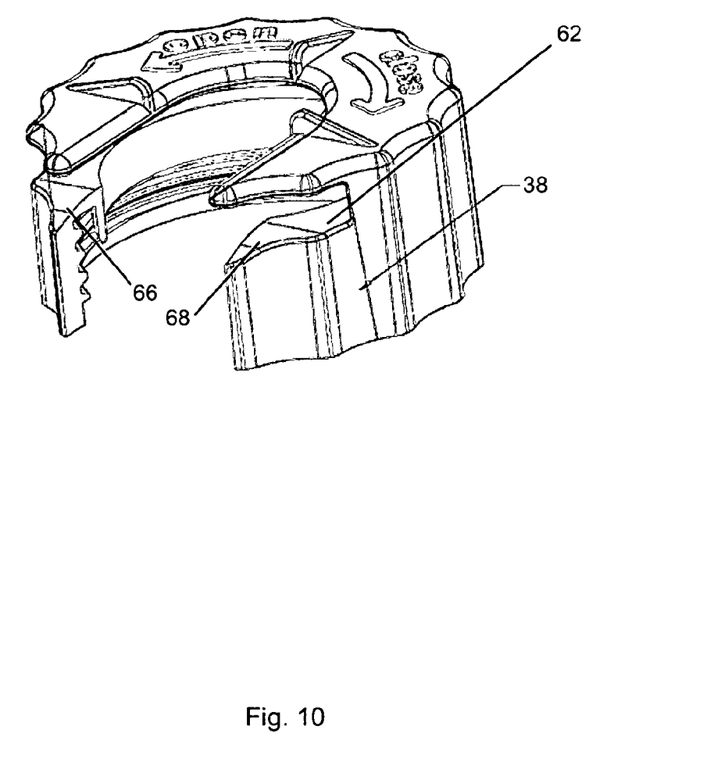
FIG. 10 shows an enlarged detail of the rotatable closure according to FIG. 9.

Compared to the embodiment according to FIGS. 1 to 3 and FIGS. 4 to 8, the only real difference in the embodiment according to FIGS. 9 and 10 lies in a differently configured closure piece 38 in the form of a rotatable closure. For simplicity, however, the closure piece 38, like the rest of the elements of this embodiment, is provided with the same reference number.

Specifically, the further embodiment in FIGS. 9 and 10 also comprises a holder 10 for receiving an injection syringe 18. The holder 10 again has a seat 16, which receives a substantially cylindrically symmetrical syringe body 20 for example, and a housing 12 which has a main body with an interior surface 121, and toward the bottom has a radially widening and, for example, conically extending stand 14. In the axial direction, which runs substantially in the vertical direction in FIGS. 9 and 10, the syringe 18 that come to lie in the seat 16 bears, with its retaining projections 28 protruding radially from the syringe body 20, either on the upper end portions of the retaining wings 52, 54 (in the case of small syringes) and/or in the slit 62 of the closure 38 (in the case of large syringes).

In the embodiment shown here, the two retaining wings 52, 54 arranged inside the seat 16 have a common pivot axle 56. The spring elements 76 acting on the retaining wings 52, 54 are, like the crosspieces 50 for receiving the pivot axle 56, not explicitly shown in FIG. 9. It can be clearly seen, however, that the retaining wings 52, 54 are once again concave in part, so as to be able in particular to form a press fit 60 with the substantially cylindrical syringe body 20. Here too, the radial end portion of the retaining wings 52, 54 lying at a distance from the pivot axle 56 is designed protruding radially outward, in order to facilitate the engagement of the syringe body 20.

FIG. 10 shows the rotatable closure 38 in more detail. In this case, the closure has a screw thread for securing the closure 38 on the housing 12, and a slit 62 which lies approximately at the height of the upper end portions of the retaining wings 52, 54 and extends about the entire closure 38 and into which the diametrically opposite retaining projections 28 of the syringe body 20 can be inserted in the radial direction. To permit easy insertion, the slit 62 can be provided with two insertion bevels 66, 68.

If, for example, the syringe is pressed into the seat 16 of this embodiment, this kind of radially inwardly directed movement of the syringe body 20 once again causes the retaining wings 52, 54 to pivot open. As soon as the syringe 18 reaches its end position, the retaining wings 52, 54 pivot radially inward again. By this means, and by partial rotation of the closure 38, it is possible to produce a sufficient press fit 60 between retaining wings 52, 54 and syringe body 20 and to securely fix the syringe in the holder 10 in the axial and radial directions of this embodiment.

LIST OF REFERENCE SIGNS 10 holder
12 housing
14 stand
16 seat
18 syringe
20 syringe body
22 syringe plunger
24 pressing piece
26 outlet
28 retaining projection
30 contact flange
32 grip surface
34 web
36 through-opening
38 closure
39 locking means
40 mating locking means
42 closure segment
44 closure segment
46 toothed surface
48 toothed surface
50 crosspiece
52 retaining wing
53 end portion
54 retaining wing
55 end portion
56 axle
58 pivot axle
60 press fit
62 slit
64 slit
66 insertion bevel
68 insertion bevel
70 bending axis
72 beveled surface
74 beveled surface
76 torsion spring
78 pivot axle
80 bearing
82 peg
84 peg

The invention claimed is:

1. A holder for an injection syringe, comprising:
a housing configured to receive the injection syringe, the housing comprising:
a main body with an interior surface defining a space for receiving the injection syringe;
a stand for placing on a supporting surface; and
a pair of retaining wings accommodated in the main body, pivotably connected to the interior surface of the main body of the housing, and configured to clamp the injection syringe for axially and/or radially fixing the injection syringe in the housing; and
a closure element connected to the housing and operable between an open position and a closed position,
wherein the pair of retaining wings are configured in such a way that a distal end of an outlet of the injection syringe, when the injection syringe is fixed in the housing by the pair of retaining wings and the closure element, faces the stand, and is positioned inward, toward the main body, of a distal end of the stand at a distance in an axial direction,
wherein the main body is a partial cylindrical sleeve with an elongated slot, and the pair of retaining wings is positioned, in its entirety, within the partial cylindrical sleeve without protruding out of the elongated slot, the pair of retaining wings respectively pivoting about a pivot axis extending in the axial direction, and
wherein the main body includes a grip surface on an exterior thereof, and radially widens toward the stand.

2. The holder as claimed in claim 1, wherein the housing, at an upper end portion thereof directed away from the stand, has a radially outwardly protruding contact flange, the radially outwardly protruding contact flange extending around at least part of a periphery of the upper end portion of the housing.

3. The holder as claimed in claim 1, wherein the housing has a radially accessible seat for insertion of the injection syringe into the housing.

4. The holder as claimed in claim 3, wherein the pair of retaining wings define the radially accessible seat.

5. The holder as claimed in claim 4, wherein the pair of retaining wings are mounted on a pivot axle extending substantially parallel to the axial direction, and at least one torsion spring is attached to the pair of retaining wings.

6. The holder as claimed in claim 4, wherein the pair of retaining wings extends parallel to each other and are configured in such a way that the radially accessible seat permits insertion of a syringe of variable size.

7. The holder as claimed in claim 4, wherein at least one of the pair of retaining wings has at least in part, in a plane perpendicular to the axial direction, a curvature adapted to a body of the injection syringe.

8. The holder as claimed in claim 5, wherein at least one of the pair of retaining wings, at an end portion opposite the pivot axle, has a substantially radially outwardly protruding end portion functioning as an insertion aid for the injection syringe.

9. The holder as claimed in claim 3, wherein the radially accessible seat can be closed by the closure element mounted pivotably or rotatably on the housing.

10. The holder as claimed in claim 9, wherein the closure element is configured to be rotatable about the axial direction in relation to the housing, and wherein the closure element is further configured with an area which, after partial rotation about a longitudinal direction of the syringe, fixes the injection syringe in the radially accessible seat of the housing.

11. The holder as claimed in claim 9, wherein the closure element is configured to rotate perpendicularly with respect to the axial direction of the holder and about a longitudinal axis of the syringe.

12. The holder as claimed in claim 9, wherein the closure element is a one-piece screw cap.

13. The holder as claimed in claim 1, wherein at least one of the pair of retaining wings, the housing, and the closure piece has, at an upper end portion thereof directed away from the stand, at least one slit or a bearing for a radially outwardly protruding retaining projection of the injection syringe, in order to fix the injection syringe axially on the holder, at least in an injection direction.

14. The holder as claimed in claim 1, wherein the pair of retaining wings respectively pivot about a common pivot axis.

15. The holder as claimed in claim 1, wherein the stand has a conical shape.

16. The holder as claimed in claim 1, wherein the closure element includes an opening in alignment with the elongated slot when in the open position.

* * * * *